United States Patent
Wimmer

(10) Patent No.: US 6,238,605 B1
(45) Date of Patent: May 29, 2001

(54) LOW-FIBRILLATION MOULDED BODIES

(75) Inventor: Adalbert Wimmer, Vocklabruck (AT)

(73) Assignee: Lenzing Aktiengesellschaft, Lenzing (AT)

( * ) Notice: Subject to any disclaimer, the term of this patent is extended or adjusted under 35 U.S.C. 154(b) by 0 days.

(21) Appl. No.: 09/290,641

(22) Filed: Apr. 12, 1999

Related U.S. Application Data

(63) Continuation of application No. PCT/AT97/00215, filed on Oct. 9, 1997.

(30) Foreign Application Priority Data

Oct. 11, 1996 (AT) .................................................... 1798/96

(51) Int. Cl.$^7$ ................................ D01F 6/12; D02G 1/02; D02G 3/38

(52) U.S. Cl. ............................. 264/103; 57/295; 57/310; 264/127; 264/129; 264/171.1; 264/175; 264/288.4; 264/290.5

(58) Field of Search .................................... 264/103, 127, 264/129, 171.1, 175, 288.4, 290.5; 57/295, 310

(56) References Cited

U.S. PATENT DOCUMENTS

| | | |
|---|---|---|
| 3,953,566 | 4/1976 | Gore . |
| 4,996,056 | 2/1991 | Blass . |
| 5,167,890 | 12/1992 | Sasshofer et al. . |
| 5,209,251 | 5/1993 | Curtis et al. . |
| 5,220,932 | 6/1993 | Blass . |
| 5,262,234 * | 11/1993 | Minor et al. ...................... 264/127 X |
| 5,357,990 | 10/1994 | Suhonen et al. . |
| 5,518,012 | 5/1996 | Dolan et al. . |
| 5,657,779 * | 8/1997 | Blass et al. .......................... 132/321 |
| 5,800,823 * | 9/1998 | Blass ................................... 424/400 |
| 5,804,290 | 9/1998 | Marini et al. . |

FOREIGN PATENT DOCUMENTS

| | | |
|---|---|---|
| 370673 | 3/1974 | (AT) . |
| 399882 | 3/1993 | (AT) . |
| 0172671 | 2/1986 | (EP) . |
| 0335466 | 10/1989 | (EP) . |
| 0391887 | 10/1990 | (EP) . |
| 0358363 | 10/1992 | (EP) . |
| 2025835 | 1/1980 | (GB) . |
| 9302633 | 2/1993 | (WO) . |
| 9534252 | 12/1995 | (WO) . |

\* cited by examiner

*Primary Examiner*—Leo B. Tentoni
(74) *Attorney, Agent, or Firm*—Baker Botts L.L.P.

(57) ABSTRACT

The invention relates to a process for the production of a low-fibrillation moulded body containing polytetrafluorethylene. The process is characterised in that a pre-moulded body of polytetrafluorethylene is twisted and then pressed flat. The pre-moulded body can be twisted around itself or around another material e.g. a mono- or multifilament or a spun yarn. The invention relates furthermore to a low fibrillation moulded body containing polytetrafluorethylene which can be obtained by means of the process in accordance with the invention and the use of the moulded body in accordance with the invention as dental floss.

45 Claims, No Drawings

LOW-FIBRILLATION MOULDED BODIES

This application is a continuation of PCT application PCT/AT97/00215 filed Oct. 9, 1997 which is incorporated by reference herein.

BACKGROUND OF THE INVENTION

The invention relates to a process for the production of a low-fibrillation moulded body containing polytetrafluorethylene, low-fibrillation moulded bodies, which can be obtained as a result of the process in accordance with the invention and the use of these as dental floss.

Polytetrafluorethylene (PTFE) is a prized material due to its thermal stability and chemical inertness. Monoaxially stretched films made from sintered PTFE are known from AT-B 370.673, the strength of which has values of between 50 N/mm$^2$ and 140 N/mm$^2$ in the stretching direction. Said films are produced when PTFE powder is first of all pressed to a cylindrical moulded body. The moulded body is then sintered, whereupon films are peeled off, heated to temperatures of at least 327 C and stretched.

GB-A 2 025 835 describes the production of porous PTFE moulded bodies in accordance with the paste extrusion process whereby a paste-like mass, which basically comprises PTFE powder and a lubricant (hydrocarbon), is pressed through dies whereby the lubricant is removed by drying. The moulded body is then heated to above the crystallite melting point of the PTFE (327° C.) and stretched during heating.

EP-A 0 391 887 describes a process for the production of a monoxially stretched moulded body of PTFE, in which a paste-like PTFE mass is continuously processed to a moulded body which is led over a number of rollers or cylinders, heated and stretched, the moulded body being heated to a temperature between 327° C. and 450° C. before applying the stretching and sintered. This process allows the production of a monoaxially stretched moulded bodies of PTFE with tenacity values in the stretching direction of at least 22 cN/tex (500 N/mm$^2$).

Furthermore, it is known that moulded bodies of PTFE can be made available with different filling substances. Moulded bodies of this kind containing filling substances are for example known from AT-B399 882 and contain talc and/or mica and/or a high temperature resistant polyimide of between 20 and 30 wt. % as a filling material. The PTFE moulded bodies described in AT-B 399 882 containing filling materials are for example suitable for use as dental floss.

Dental flosses of PTFE tapes are moreover described in EP-A 0 335 466, U.S. Pat. No. 5,209,251 and U.S. Pat. No. 5,220,932. The PTFE-tapes can have different densities and can be in a folded or unfolded state.

Compared to conventional dental flosses e.g. of polyamide, the PTFE material is softer which means greater suppleness and softness which results in a lower risk of hurting the flesh of the gums when in use.

Since they are in a stretched or expanded state, PTFE tapes tend to fibrillate which means that individual fibres split. This leads to problems either when unreeling the dental floss from the dental floss dispenser respectively when the dental floss splits when in use leaving traces of dental floss between the teeth.

In PCT-WO 95/34252 a dental floss is suggested from an unfolded expanded PTFE fibre which has a regular thickness and width overall whereby the parallel placed edges of the dental floss are resistant to fibrillation. In this respect a thicker PTFE sheet in comparison to state of the art is cut into equally thick and broad strands. The strands are rolled up without prior folding.

SUMMARY OF THE INVENTION

The present invention sets itself the task of providing a moulded body containing PTFE, which is particularly well suited as a dental floss material, and a process for the production thereof whereby the moulded body is to be particularly resistant to fibrillation. The process for the production of the moulded body should be both simple and cheap.

The task of the present invention is solved by a process for the production of a low-fibrillation moulded body containing polytetrafluorethylene characterised in that a pre-moulded body of polytetrafluorethylene is twisted and then pressed flat.

Surprisingly it has been shown that as a result of the measure of twisting a pre-moulded body containing PTFE and then pressing the twisted pre-moulded body flat again, moulded bodies can be obtained which are particularly resistant to fibrillation. The process in accordance with the invention is characterised in that it can be easily performed. The process in accordance with the invention can also be performed continuously.

DETAILED DESCRIPTION OF THE PREFERRED EMBODIMENTS

For the purpose of the present invention by "pre-moulded bodies" moulded bodies produced according to the known methods of state of the art, e.g. a fibre or a tape, are meant.

Compared to PTFE products folded according to state of the art, the pre-moulded body in the present invention is not folded but rather completely twisted respectively twined.

In this respect it has shown itself to be advantageous when the pre-moulded body is twisted with 30 twists per m (T/m) up to 400 twists per m (T/m).

The pre-moulded body can preferably be twisted around itself. In this case it is favourable when the pre-moulded body is twisted by 220 twists per m up to 270 twists per m, and preferably 245 twists per m up to 255 twists per m. In the case of a pre-moulded body mainly comprising PTFE this results in a moulded body mainly comprising PTFE.

One preferred embodiment of the process in accordance with the invention is characterised in that the pre-moulded body of polytetrafluorethylene is twisted around another material. This other material can preferably be for example a mono- or multifilament, preferably of polyamide, polyester or yet again polytetrafluoroethylene. The other material can be a spun yarn, preferably of cotton, viscose, polyamide, polyester or acrylic.

With this embodiment of the process in accordance with the invention it becomes possible, to combine the properties of the twisted other material, e.g. a higher strength, with the advantageous properties of PTFE, particularly suppleness and the good gliding property.

The titre of the other material preferably lies in the range between 100 dtex and 1000 dtex, preferably between 300 dtex and 500 dtex.

When the pre-moulded body of PTFE is twisted around another material, it is advantageous that the pre formed body is twisted around the other material with 50 twists per m to 250 twists per m, preferably 100 twists per m up to 150 twists per m.

One other advantageous embodiment of the process in accordance with the invention is when the other material contains flavourings and/or substances which serve dental hygiene. It is known that PTFE moulded bodies, particularly when they are used as dental floss, contain flavourings and/or substances which serve dental hygiene. Materials which can be used for this are e.g. described in PCT-WO 95/34252.

It has proven itself favourable when additives of this kind are contained in the other material around which the pre-moulded bodies are twisted. These additives can for example serve as a depot.

The twisted pre formed body is preferably pressed flat as a result of calendering preferably between two rolls. In this mode of operation in particular it is possible to continuously perform the process in accordance with the invention.

The pre-moulded body used is preferably a monoaxially stretched moulded body of PTFE. The pre-moulded body can preferably be in the shape of a tape prior to twisting. The titre of the pre-moulded body can be between 400 dtex to 1800 dtex, and preferably 600 dtex to 1200 dtex.

Monoaxially stretched pre-moulded bodies are particularly well suited to the process in accordance with the invention which have a tenacity value in the stretching direction of at least 20 cN/tex, and preferably 25 cN/tex to 30 cN/tex, and a density of less than 2 $g/cm^3$, preferably of less than 1.8 $g/cm^3$, and in particular from 1.6 $g/cm^3$ to 1.8 $g/cm^3$. Such pre-moulded bodies of this kind can for example be produced in a similar way to the processes described in EP 0 391 887 A1 or U.S. Pat. No. 3,953,566.

It appears to be favourable when the pre-moulded body contains flavourings and/or substances which serve dental hygiene.

For use as dental floss in particular it is advantageous when a coating of wax is applied to the moulded body obtained by means of the processes in accordance with the invention. The wax applied to the moulded body can also obtain flavourings and/or substances which serve dental hygiene.

The task of the present invention is also solved by a low-fibrillation moulded body containing polytetrafluoroethylene which is obtainable using the process in accordance with the invention.

The moulded bodies in accordance with the invention prove to be particularly resistant to fibrillation and have in this respect better properties than moulded bodies according to state of the art. As a result of twisting, the surface and especially the edges of the moulded body are slightly rougher. This produces a better cleansing effect, particularly when using the moulded body in accordance with the invention as dental floss, than with known untwisted materials.

Thus the moulded bodies in accordance with the invention are particularly well suited as a material for dental floss where the properties desired by the user of a dental floss, namely suppleness on the one hand and tenacity and resistance to fibrillation on the other in connection with a good cleansing effect, are particularly well satisfied.

EXAMPLES

Example 1
Twisted and Calendered PTFE Tape:

A PTFE tape with a width of 2.2 mm, a thickness of 35 µm, a tenacity of 27 cN/tex, 7% elongation and a density of 1.8 $g/cm^3$ was twisted with 250 twists per m (T/m) and finally pressed flat between two rolls to tape form. One obtains a tape with a thickness of 50 µm, a width of 1,3 mm and a density of 1.9 $g/cm^3$. The tenacity equals 25 cN/tex with an elongation of 10%.

Example 2a
Twisting Round a Polyester Multifilament Yarn:

A polyester multifilament yarn (320 dtex) is covered with a PTFE tape of 800 dtex with 100 T/m. This is done on a ring twisting machine by setting the thread tension of the materials fed at different settings (PET yarn 100 g, PTFE tape 20 g).

The obtained yarn covered with PTFE tape is pressed flat as described in example 1. One obtains a tape with a width of 1.5 mm and a thickness of 50 µm. The tear strength equals 35 N with a twist of 15%.

Example 2b
Twist Around a Polyamide Multifilament Yarn:

As in example 2a, however using a polyamide multifilament yarn of 480 dtex, covered with the PTFE tape.

The tape obtained has an overall titre of 1300 dtex with a width of 1.5 mm and a thickness of 55 µm. This tape is prepared with 10% bee's wax.

Example 2c
Twisting Round a Spun Yarn:

A cotton spun yarn with 500 dtex is covered with a PTFE tape of 800 dtex according to example 2a and then pressed flat.

One obtains a tape with a width of 1.5 mm, a thickness of 60 µm and 30 N tear strength. This tape is prepared with 8% bee's wax which contains 1% peppermint oil.

Example 3a
Use of Additives and/or Substances Which Serve Dental Hygiene:

The process is the same as in example 2a, however, the polyester multifilament yarn is immersed in 3% disinfectant prior to twisting with the PTFE tape.

Example 3b

The process is the same as in example 2c, however, a citrus flavour is added to the cotton yarn prior to twisting with the PTFE tape.

What is claimed is:

1. Process for the preparation of a low-fibrillation moulded body comprising polytetrafluoroethylene comprising:
   providing a pre-moulded body of polytetrafluoroethylene;
   twisting the pre-moulded body; and
   subsequently pressing the pre-moulded body to flatten the pre-moulded body thereby forming a moulded body which exhibits reduced fibrillation.

2. Process according to claim 1 comprising twisting the pre-moulded body so as to form from 30 twists to 400 twists per meter.

3. Process according to claim 1 or claim 2 comprising twisting the pre-moulded body around itself.

4. Process according to claim 3 comprising twisting the pre-moulded body so as to form 220 twists to 270 twists per meter.

5. Process according to claim 4 comprising twisting the pre-moulded body so as to form 245 twists to 255 twists per meter.

6. Process according to claim 1 or claim 2 comprising twisting the pre-moulded body around another body.

7. Process according to claim 6 wherein said another body is in the form of one selected from the group consisting of a monofilament and a multifilament.

8. Process according to claim 7 wherein said another body comprises material selected from the group consisting of polyamide, polyester and polytetrafluoroethylene.

9. Process for the preparation of a low-fibrillation moulded body comprising polytetrafluoroethylene comprising:
   providing a pre-moulded body of polytetrafluoroethylene;
   twisting the pre-moulded body around another body wherein said another body is in the form of spun yarn; and
   pressing the pre-moulded body to flatten the pre-moulded body thereby forming a moulded body which exhibits reduced fibrillation.

10. Process according to claim 9 wherein said another body comprises a material selected from the group consisting of cotton, viscose, polyamide, polyester and acrylic.

11. Process according to claim 6 wherein said another body includes material having a titre in the range of between 100 decitex and 1000 decitex.

12. Process according to claim 11 wherein said another body includes material having a titre in the range of between 300 decitex and 500 decitex.

13. Process for the preparation of a low-fibrillation moulded body comprising polytetrafluoroethylene comprising:
   providing a pre-moulded body of polytetrafluoroethylene;
   twisting the pre-moulded body around another body so as to form 50 twists to 250 twists per meter; and
   pressing the pre-moulded body to flatten the pre-moulded body thereby forming a moulded body which exhibits reduced fibrillation.

14. Process according to claim 13 comprising twisting the pre-moulded body so as to form 100 twists to 150 twists per meter.

15. Process for the preparation of a low-fibrillation moulded body comprising polytetrafluoroethylene comprising:
   providing a pre-moulded body of polytetrafluoroethylene;
   twisting the pre-moulded body around another body; and
   pressing the pre-moulded body to flatten the pre-moulded body thereby forming a moulded body which exhibits reduced fibrillation;
   wherein said another body includes material comprising at least one selected from the group consisting of flavorings suitable for use in dental hygiene products and nonflavoring substances suitable for use in dental hygiene products.

16. Process according to claim 1 comprising pressing the pre-moulded body flat by calendering.

17. Process according to claim 6 comprising pressing the premoulded body flat by calendering.

18. Process according to claim 16 comprising pressing the premoulded body flat by calendering between two rolls.

19. Process according to claim 17 comprising pressing the premoulded body flat by calendering between two rolls.

20. Process according to claim 1 comprising providing a pre-moulded body which has been monoaxially stretched.

21. Process for the preparation of a low-fibrillation moulded body comprising polytetrafluoroethylene comprising:
   providing a pre-moulded body which has been monoaxially stretched;
   twisting the pre-moulded body around another body; and
   pressing the pre-moulded body to flatten the pre-moulded body thereby forming a moulded body which exhibits reduced fibrillation.

22. Process according to claim 1 wherein the pre-moulded body is in the form of a tape prior to twisting.

23. Process according to claim 6 wherein the pre-moulded body is in the form of a tape prior to twisting.

24. Process according to claim 1 wherein the titre of the pre-moulded body is 400 decitex to 1800 decitex prior to twisting.

25. Process according to claim 6 wherein the titre of the pre-moulded body is 400 decitex to 1800 decitex prior to twisting.

26. Process according to claim 24 wherein the titre of the pre-moulded body prior to twisting is 600 decitex to 1200 decitex.

27. Process according to claim 25 wherein the titre of the pre-moulded body prior to twisting is 600 decitex to 1200 decitex.

28. Process according to claim 20 wherein the monoaxially stretched pre-moulded body has a tenacity value in the stretching direction of at least 20 cN/tex and density of less than 2 $g/cm^3$.

29. Process according to claim 21 wherein the monoaxially stretched pre-moulded body has a tenacity value in the stretching direction of at least 20 cN/tex and density of less than 2 $g/cm^3$.

30. Process for the preparation of a low-fibrillation moulded body comprising polytetrafluoroethylene comprising the steps of:
   providing a pre-moulded body which has been monoaxially stretched;
   twisting the pre-moulded body; and
   pressing the pre-moulded body to flatten the pre-moulded body thereby forming a moulded body which exhibits reduced fibrillation wherein the monoaxially stretched pre-moulded body has a tenacity value in the stretching direction of 25 cN/tex to 30 cN/tex and a density of less than 2 $g/cm^3$.

31. Process according to claim 29 wherein the monoaxially stretched pre-moulded body has a tenacity value in the stretching direction of 25 cN/tex to 30 cN/tex.

32. Process according to claim 28 wherein the monoaxially stretched pre-moulded body has a density of less than 1.8 $g/cm^3$.

33. Process according to claim 29 wherein the monoaxially stretched pre-moulded body has a density of less than 1.8 $g/cm^3$.

34. Process for the preparation of a low-fibrillation moulded body comprising polytetrafluoroethylene comprising the steps of:
   providing a pre-moulded body which has been monoaxially stretched;
   twisting the pre-moulded body; and
   pressing the pre-moulded body to flatten the pre-moulded body thereby forming a moulded body which exhibits reduced fibrillation wherein the monoaxially stretched pre-moulded body has density of 1.6 $g/cm^3$ to 1.8 $g/cm^3$ and a tenacity value with the stretching direction of at least 20 cN/tex.

35. Process according to claim 29 wherein the monoaxially stretched pre-moulded body has density of 1.6 $g/cm^3$ to 1.8 $g/cm^3$.

36. Process for the preparation of a low-fibrillation moulded body comprising polytetrafluoroethylene comprising:
   providing a pre-moulded body;
   twisting the pre-moulded body around another body;
   pressing the pre-moulded body to flatten the pre-moulded body thereby forming a moulded body which exhibits reduced fibrillation, and
   applying a wax coating to said moulded body which exhibits reduced fibrillation.

37. Process according to claim 28 further comprising applying a wax coating to said moulded body which exhibits reduced fibrillation.

38. Process for the preparation of a low-fibrillation moulded body comprising polytetrafluoroethylene comprising:

providing a pre-moulded body of polytetrafluoroethylene;

twisting the pre-moulded body so as to form from 30 to 400 twists per meter around another body wherein said another body is in the form of spun yarn; and pressing the pre-moulded body to flatten the pre-moulded body thereby forming a moulded body which exhibits reduced fibrillation.

39. Process for the preparation of a low-fibrillation moulded body comprising polytetrafluoroethylene comprising:

providing a pre-moulded body of polytetrafluoroethylene;

twisting the pre-moulded body around another body so as to form from 30 to 400 twists per meter wherein said another body is in the form of spun yarn; and pressing the pre-moulded body to flatten the pre-moulded body thereby forming a moulded body which exhibits reduced fibrillation.

40. Process for the preparation of a low-fibrillation moulded body comprising polytetrafluoroethylene comprising:

providing a pre-moulded body of polytetrafluoroethylene;

twisting the pre-moulded body around another body so as to form from 30 to 400 twists per meter; and pressing the pre-moulded body to flatten the pre-moulded body thereby forming a moulded body which exhibits reduced fibrillation wherein said another body includes material comprising at least one selected from the group consisting flavorings suitable for use in dental hygiene products and nonflavoring substances suitable for use in dental hygiene products.

41. Process for the preparation of a low-fibrillation moulded body comprising polytetrafluoroethylene comprising:

providing a pre-moulded body which has been monoaxially stretched;

twisting the pre-moulded body around another body so as to form from 30 to 400 twists per meter; and pressing the pre-moulded body to flatten the pre-moulded body thereby forming a moulded body which exhibits reduced fibrillation.

42. Process for the preparation of a low-fibrillation moulded body comprising polytetrafluoroethylene comprising:

providing a pre-moulded body which has been monoaxially stretched;

twisting the pre-moulded body around another body so as to form from 30 to 400 twists per meter; and pressing the pre-moulded body to flatten the pre-moulded body thereby forming a moulded body which exhibits reduced fibrillation wherein the monoaxially stretched pre-moulded body has a tenacity value in the stretching direction of at least 20 cN/tex and density of less than 2 g/cm$^3$.

43. Process for the preparation of a low-fibrillation moulded body comprising polytetrafluoroethylene comprising the steps of:

providing a pre-moulded body which has been monoaxially stretched;

twisting the pre-moulded body around another body so as to form from 30 to 400 twists per meter; and pressing the pre-moulded body to flatten the pre-moulded body thereby forming a moulded body which exhibits reduced fibrillation wherein the monoaxially stretched pre-moulded body has a tenacity value in the stretching direction of 25 cN/tex to 30 cN/tex and a density of less than 2 g/cm$^3$.

44. Process for the preparation of a low-fibrillation moulded body comprising polytetrafluoroethylene comprising the steps of:

providing a pre-moulded body which has been monoaxially stretched;

twisting the pre-moulded body around another body so as to form from 30 to 400 twists per meter; and pressing the pre-moulded body to flatten the pre-moulded body thereby forming a moulded body which exhibits reduced fibrillation wherein the monoaxially stretched pre-moulded body has a density of less than 1.8 g/cM$^3$ and a tenacity value with the stretching direction of at least 20 cN/tex.

45. Process for the preparation of a low-fibrillation moulded body comprising polytetrafluoroethylene comprising the steps of:

providing a pre-moulded body which has been monoaxially stretched;

twisting the pre-moulded body around another body so as to form from 30 to 400 twists per meter; and pressing the pre-moulded body to flatten the pre-moulded body thereby forming a moulded body which exhibits reduced fibrillation wherein the monoaxially stretched pre-moulded body has density of 1.6 g/cm$^3$ to 1.8 g/cm$^3$ and a tenacity value with the stretching direction of at least 20 cN/tex.

* * * * *

UNITED STATES PATENT AND TRADEMARK OFFICE
CERTIFICATE OF CORRECTION

PATENT NO. : 6,238,605 B1
DATED : May 29, 2001
INVENTOR(S) : Wimmer et al.

It is certified that error appears in the above-identified patent and that said Letters Patent is hereby corrected as shown below:

Title page,
ABSTRACT,
Lines 2-3, "polytetrafluorethylene" should read -- polytetrafluoroethylene --
Line 4, "polytetrafluorethylene" should read -- polytetrafluoroethylene --
Line 8, "polytetrafluorethylene" should read -- polytetrafluoroethylene --

Column 1,
Line 10, "polytetrafluorethylene" should read -- polytetrafluoroethylene --
Line 13, "Polytetrafluorethylene" should read -- Polytetrafluoroethylene --
Line 21, "327 C" should read -- 327° C --
Line 29, "crystallite" should read -- crystalline --
Line 32, "monoxially" should read -- monoaxially --
Line 38, "a" should be deleted Column 2,
Line 15, "polytetrafluorethylene" should read -- polytetrafluoroethylene --
Line 16, "polytetrafluorethylene" should read -- polytetrafluoroethylene --
Line 46, "polytetrafluorethylene" should read -- polytetrafluoroethylene --
Line 47, "polytetrafluorethylene" should read -- polytetrafluoroethylene --
Line 61, "pre formed" should read -- pre-formed --

Column 3,
Line 11, "pre formed" should read -- pre-formed --
Line 37, "obtain" should read -- contain --
Lines 40-41, "polytetrafluorethylene" should read -- polytetrafluoroethylene --
Line 67, "1,3 mm" should read -- 1.3 mm --

UNITED STATES PATENT AND TRADEMARK OFFICE
CERTIFICATE OF CORRECTION

PATENT NO.  : 6,238,605 B1
DATED       : May 29, 2001
INVENTOR(S) : Wimmer et al.

It is certified that error appears in the above-identified patent and that said Letters Patent is hereby corrected as shown below:

Column 4,
Line 43, "What is claimed is:" should read -- I claim: --

Column 7,
Line 32, "consisting flavorings" should read -- consisting of flavorings --

Column 8,
Line 32, "$g/cM^3$" should read -- $g/cm^3$ --

Signed and Sealed this

Twenty-sixth Day of March, 2002

Attest:

JAMES E. ROGAN
Attesting Officer     Director of the United States Patent and Trademark Office